(12) United States Patent
Paullin et al.

(10) Patent No.: US 9,139,718 B2
(45) Date of Patent: Sep. 22, 2015

(54) PREPARATION OF POLY ALPHA-1,3-GLUCAN ETHERS

(71) Applicant: E I DU PONT DE NEMOURS AND COMPANY, Wilmington, DE (US)

(72) Inventors: Jayme L Paullin, Claymont, DE (US); Andrea M Perticone, Wilmington, DE (US); Rahul B Kasat, Wilmington, DE (US); T Joseph Dennes, Parkesburg, PA (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 23 days.

(21) Appl. No.: 14/107,067

(22) Filed: Dec. 16, 2013

(65) Prior Publication Data

US 2014/0179913 A1 Jun. 26, 2014

Related U.S. Application Data

(60) Provisional application No. 61/740,087, filed on Dec. 20, 2012.

(51) Int. Cl.
| | |
|---|---|
| *C08B 37/00* | (2006.01) |
| *C08B 37/18* | (2006.01) |
| *C08L 5/00* | (2006.01) |
| *C12P 19/18* | (2006.01) |
| *C12P 19/04* | (2006.01) |

(52) U.S. Cl.
CPC ............... *C08L 5/00* (2013.01); *C08B 37/0009* (2013.01); *C12P 19/04* (2013.01); *C12P 19/18* (2013.01)

(58) Field of Classification Search
None
See application file for complete search history.

(56) References Cited

U.S. PATENT DOCUMENTS

| 7,000,000 B1 | 2/2006 | O'Brien |
| 2006/0134417 A1 | 6/2006 | Takaha et al. |
| 2013/0244287 A1 | 9/2013 | O'Brien et al. |
| 2013/0244288 A1 | 9/2013 | O'Brien et al. |

FOREIGN PATENT DOCUMENTS

CN 1283633 A 2/2001

OTHER PUBLICATIONS

Bao, X. et al "Chemical modifications of the (1-3)-alpha-D-glucan . . . " Carbohyd. Res. (2001) vol. 336, pp. 127-140.*
Machine Translation, CN1283633, Carboxynethylated Derivative of Ganoderic Alpha-(1,3)D-Glucosan and Its Usage and Preparing Process, Wuhan University, Feb. 14, 2001.
Cantarel et al., The Carbohydrate-Active Enzymes Database (CAZY): An Expert Resource for Glycogenomics, Nucleic Acids Research (2009), vol. 37, Database Issue, pp. D233-D238.
Kiho et al., (1-->3)-α-D-Glucan From an Alkaline Extract of Agrocybe Cylindracea, and Antitumor Activity of Its O-(Carboxy-Methyl)ated Derivatives, Carbohydrate Research (1989), vol. 189, pp. 273-279.
Ogawa et al., Crystal Structure of (1-->3)-α-D-Glucan, in Fiber Defraction Methods, ACS Symposium (1980), vol. 47, pp. 353-362.
Ogawa et al., X-Ray Diffraction Data for (1-->3)-α-D-Glucan Triacetate, Carbohydrate Poymers (1983), vol. 3, pp. 287-297.
Simpson et al., Four Glucosyltransferases, GTFJ, GTFK, GTFL and GTFM, From *Streptococcus salivarious* ATCC 25975, Microbiology (1995), vol. 141, pp. 1451-1460.
Yui et al., Molecular and Crystal Structure of (1-->3)-α-D-Glucan Triacetate, Int. J. Biol. Macromol. (1992), vol. 14, pp. 87-96.
Shida et al., A (1/AR3)-Alpha-D-Glucan Isolated From the Fruit Bodies of Lentinus Edodes, Carbohydrate Research (1978), vol. 60, No. 1, pp. 117-127.
Internationl Search Report, Corresponding PCT Application, International Patent Application No. PCT/US2013/075285, Mailed Mar. 3, 2014.

* cited by examiner

*Primary Examiner* — Leigh Maier

(57) ABSTRACT

Poly alpha-1,3-glucan ether compounds are disclosed herein with a degree of substitution of about 0.05 to about 3.0. Also disclosed are methods of producing poly alpha-1,3-glucan ether compounds.

18 Claims, No Drawings

PREPARATION OF POLY ALPHA-1,3-GLUCAN ETHERS

This application claims the benefit of U.S. Provisional Application Nos. 61/740,076; 61/740,087; 61/740,106; 61/740,119 and 61/740,127; each filed Dec. 20, 2012, all of which are incorporated herein by reference in their entirety.

FIELD OF INVENTION

This invention is in the field of poly alpha-1,3-glucan derivatives. Specifically, this invention pertains to poly alpha-1,3-glucan ethers and methods of their preparation.

BACKGROUND

Driven by a desire to find new structural polysaccharides using enzymatic syntheses or genetic engineering of microorganisms or plant hosts, researchers have discovered polysaccharides that are biodegradable, and that can be made economically from renewable resource-based feedstocks. One such polysaccharide is poly alpha-1,3-glucan, a glucan polymer characterized by having alpha-1,3-glycosidic linkages. This polymer has been isolated by contacting an aqueous solution of sucrose with a glucosyltransferase enzyme isolated from *Streptococcus salivarius* (Simpson et al., *Microbiology* 141:1451-1460, 1995). Films prepared from poly alpha-1,3-glucan tolerate temperatures up to 150° C. and provide an advantage over polymers obtained from beta-1,4-linked polysaccharides (Ogawa et al., *Fiber Differentiation Methods* 47:353-362, 1980).

U.S. Pat. No. 7,000,000 disclosed the preparation of a polysaccharide fiber comprising hexose units, wherein at least 50% of the hexose units within the polymer were linked via alpha-1,3-glycosidic linkages using an *S. salivarius* gtfJ enzyme. This enzyme utilizes sucrose as a substrate in a polymerization reaction producing poly alpha-1,3-glucan and fructose as end-products (Simpson et al., 1995). The disclosed polymer formed a liquid crystalline solution when it was dissolved above a critical concentration in a solvent or in a mixture comprising a solvent. From this solution continuous, strong, cotton-like fibers, highly suitable for use in textiles, were spun and used.

Kiho et al. (*Carb. Res.* 189:273-270, 1989) disclosed the alkaline extraction and isolation of poly alpha-1,3-glucan from the fungus, *Agrocybe cylindracea*, which was further derivatized to sodium carboxymethylglucan (CMG). This ether derivative exhibited anti-tumor properties against sarcoma. Similarly, Zhang et al. (Intl. Publ. No. CN1283633) described the extraction of poly alpha-1,3-glucan from the medicinal fungus, *Ganoderma lucidum*, and its derivatization to CMG.

Development of new poly alpha-1,3-glucan ether derivatives and methods of preparing such derivatives is desirable given their potential utility in various applications.

SUMMARY OF INVENTION

In one embodiment, the invention concerns a composition comprising a poly alpha-1,3-glucan ether compound represented by the structure:

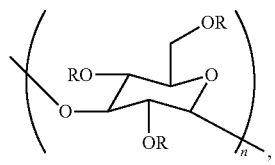

wherein
(i) n is at least 6,
(ii) each R is independently an H or an organic group, and
(iii) the compound has a degree of substitution of about 0.05 to about 3.0.

In a second embodiment, the organic group is a hydroxy alkyl group, alkyl group, or carboxy alkyl group. The compound in this embodiment may contain one type of the organic group, or two or more types of the organic group. The organic group may be a hydroxypropyl, dihydroxypropyl, hydroxyethyl, methyl, ethyl, or carboxymethyl group, for example. In a third embodiment, the compound contains one type of the organic group, whereas the compound contains two or more types of the organic group in a fourth embodiment.

In a fifth embodiment, the degree of substitution of the poly alpha-1,3-glucan ether compound is about 0.2 to about 2.0.

In a sixth embodiment, the invention concerns a method for producing a poly alpha-1,3-glucan ether compound. This method comprises contacting poly alpha-1,3-glucan in a reaction under alkaline conditions with at least one etherification agent comprising an organic group. The etherification agent is etherified to the poly alpha-1,3-glucan in this contacting step, thereby producing a poly alpha-1,3-glucan ether compound represented by the structure:

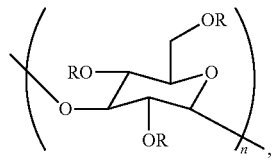

wherein
(i) n is at least 6,
(ii) each R is independently an H or the organic group, and
(iii) the compound has a degree of substitution of about 0.05 to about 3.0. A poly alpha-1,3-glucan ether produced by this method can optionally be isolated.

In a seventh embodiment, the alkaline conditions of the reaction comprise an alkali hydroxide solution.

In an eighth embodiment, the reaction comprises an organic solvent. The organic solvent is isopropanol in a ninth embodiment.

In a tenth embodiment, the contacting step of the method further comprises heating the reaction, and/or neutralizing the pH of the reaction.

In an eleventh embodiment of the method, the organic group is a hydroxy alkyl group, alkyl group, or carboxy alkyl group. The compound in this embodiment may contain one type of the organic group, or two or more types of the organic group.

In a twelfth embodiment, the poly alpha-1,3-glucan used in the method is in the form of a slurry. The slurry comprises poly alpha-1,3-glucan, sucrose, glucose, fructose and a glucosyltransferase enzyme in a thirteenth embodiment of the method.

In a fourteenth embodiment, the poly alpha-1,3-glucan used in the method is in the form of a wet cake.

DETAILED DESCRIPTION OF INVENTION

The disclosures of all patent and non-patent literature cited herein are incorporated herein by reference in their entirety.

As used herein, the term "invention" or "disclosed invention" is not meant to be limiting, but applies generally to any of the inventions defined in the claims or described herein. These terms are used interchangeably herein.

The terms "poly alpha-1,3-glucan", "alpha-1,3-glucan polymer" and "glucan polymer" are used interchangeably herein. Poly alpha-1,3-glucan is a polymer comprising glucose monomeric units linked together by glycosidic linkages, wherein at least about 50% of the glycosidic linkages are alpha-1,3-glycosidic linkages. Poly alpha-1,3-glucan is a type of polysaccharide. The structure of poly alpha-1,3-glucan can be illustrated as follows:

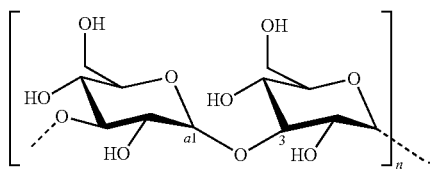

The poly alpha-1,3-glucan that can be used for preparing poly alpha-1,3-glucan ether compounds herein can be prepared using chemical methods. Alternatively, it can be prepared by extracting it from various organisms, such as fungi, that produce poly alpha-1,3-glucan. Alternatively still, poly alpha-1,3-glucan can be enzymatically produced from sucrose using one or more glucosyltransferase (gtf) enzymes (e.g., gtfJ), such as described in U.S. Pat. No. 7,000,000, and U.S. Patent Appl. Publ. Nos. 2013/0244288 and 2013/0244287 (all of which are incorporated herein by reference), for example.

The terms "glucosyltransferase enzyme", "gtf enzyme", "gtf enzyme catalyst", "gtf", and "glucansucrase" are used interchangeably herein. The activity of a gtf enzyme herein catalyzes the reaction of the substrate sucrose to make the products poly alpha-1,3-glucan and fructose. Other products (byproducts) of a gtf reaction can include glucose (where glucose is hydrolyzed from the glucosyl-gtf enzyme intermediate complex), various soluble oligosaccharides (DP2-DP7), and leucrose (where glucose of the glucosyl-gtf enzyme intermediate complex is linked to fructose). Leucrose is a disaccharide composed of glucose and fructose linked by an alpha-1,5 linkage. Wild type forms of glucosyltransferase enzymes generally contain (in the N-terminal to C-terminal direction) a signal peptide, a variable domain, a catalytic domain, and a glucan-binding domain. A gtf herein is classified under the glycoside hydrolase family 70 (GH70) according to the CAZy (Carbohydrate-Active EnZymes) database (Cantarel et al., *Nucleic Acids Res.* 37:D233-238, 2009).

The percentage of glycosidic linkages between the glucose monomer units of poly alpha-1,3-glucan used to prepare poly alpha-1,3-glucan ether compounds herein that are alpha-1,3 is at least about 50%, 60%, 70%, 80%, 90%, 95%, 96%, 97%, 98%, 99%, or 100% (or any integer value between 50% and 100%). In such embodiments, accordingly, poly alpha-1,3-glucan has less than about 50%, 40%, 30%, 20%, 10%, 5%, 4%, 3%, 2%, 1%, or 0% (or any integer value between 0% and 50%) of glycosidic linkages that are not alpha-1,3.

Poly alpha-1,3-glucan used to produce poly alpha-1,3-glucan ether compounds herein is preferably linear/unbranched. In certain embodiments, poly alpha-1,3-glucan has no branch points or less than about 10%, 9%, 8%, 7%, 6%, 5%, 4%, 3%, 2%, or 1% branch points as a percent of the glycosidic linkages in the polymer. Examples of branch points include alpha-1,6 branch points, such as those present in mutan polymer.

The terms "glycosidic linkage" and "glycosidic bond" are used interchangeably herein and refer to the type of covalent bond that joins a carbohydrate (sugar) molecule to another group such as another carbohydrate. The term "alpha-1,3-glycosidic linkage" as used herein refers to the type of covalent bond that joins alpha-D-glucose molecules to each other through carbons 1 and 3 on adjacent alpha-D-glucose rings. This linkage is illustrated in the poly alpha-1,3-glucan structure provided above. Herein, "alpha-D-glucose" will be referred to as "glucose".

The terms "poly alpha-1,3-glucan ether compound", "poly alpha-1,3-glucan ether", and "poly alpha-1,3-glucan ether derivative" are used interchangeably herein. A poly alpha-1,3-glucan ether compound herein can be represented by the structure:

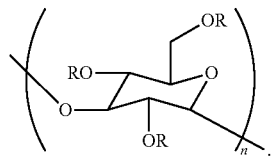

Regarding the formula of this structure, n can be at least 6, and each R can independently be a hydrogen atom (H) or an organic group. A poly alpha-1,3-glucan ether compound herein has a degree of substitution of about 0.05 to about 3.0.

A poly alpha-1,3-glucan ether compound is termed an "ether" herein by virtue of comprising the substructure —$C_G$—O—C—, where "—$C_G$—" represents carbon 2, 4, or 6 of a glucose monomeric unit of a poly alpha-1,3-glucan ether compound, and where "—C—" is comprised in the organic group.

Poly alpha-1,3-glucan ether compounds disclosed herein are synthetic, man-made compounds.

An "organic group" group as used herein refers to a chain of one or more carbons that (i) has the formula —$C_nH_{2n+1}$ (i.e., an alkyl group, which is completely saturated) or (ii) is mostly saturated but has one or more hydrogens substituted with another atom or functional group (i.e., a "substituted alkyl group"). Such substitution may be with one or more hydroxyl groups, oxygen atoms (thereby forming an aldehyde or ketone group), carboxyl groups, or other alkyl groups. In other words, where R is an organic group, R can be a chain of one or more saturated carbons, or a chain of carbons having one or more hydrogens substituted with a hydroxyl group, oxygen atom (thereby forming an aldehyde or ketone group), carboxyl group, or alkyl group.

A "hydroxy alkyl" group herein refers to a substituted alkyl group in which one or more hydrogen atoms of the alkyl group are substituted with a hydroxyl group. A "carboxy alkyl" group herein refers to a substituted alkyl group in which one or more hydrogen atoms of the alkyl group are substituted with a carboxyl group.

A "halide" herein refers to a compound comprising one or more halogen atoms (e.g., fluorine, chlorine, bromine, iodine). A halide herein can refer to a compound comprising one or more halide groups such as fluoride, chloride, bromide, or iodide. A halide group may serve as a reactive group of an etherification agent.

The terms "reaction", "reaction composition", and "etherification reaction" are used interchangeably herein and refer to a reaction comprising at least poly alpha-1,3-glucan and an etherification agent. These components are typically dissolved and/or mixed in an aqueous alkali hydroxide. A reaction is placed under suitable conditions (e.g., time, temperature) for the etherification agent to etherify one or more hydroxyl groups of the glucose units of poly alpha-1,3-glucan with an organic group, thereby yielding a poly alpha-1,3-glucan ether compound.

The term "alkaline conditions" herein refers to a solution or mixture pH of at least 11 or 12. Alkaline conditions can be prepared by any means known in the art, such as by dissolving an alkali hydroxide in a solution or mixture.

The terms "etherification agent" and "alkylation agent" are used interchangeably herein. An etherification agent herein refers to an agent that can be used to etherify one or more hydroxyl groups of the glucose units of poly alpha-1,3-glucan with an organic group. An etherification agent thus comprises an organic group.

The term "poly alpha-1,3-glucan slurry" herein refers to an aqueous mixture comprising the components of a glucosyltransferase enzymatic reaction such as poly alpha-1,3-glucan, sucrose, one or more glucosyltransferase enzymes, glucose and fructose.

The term "poly alpha-1,3-glucan wet cake" herein refers to poly alpha-1,3-glucan that has been separated from a slurry and washed with water or an aqueous solution. Poly alpha-1,3-glucan is not dried when preparing a wet cake.

The term "degree of substitution" (DoS) as used herein refers to the average number of hydroxyl groups substituted in each monomeric unit (glucose) of a poly alpha-1,3-glucan ether compound. Since there are three hydroxyl groups in each monomeric unit in poly alpha-1,3-glucan, the degree of substitution in a poly alpha-1,3-glucan ether compound herein can be no higher than 3.

The term "molar substitution" (M.S.) as used herein refers to the moles of an organic group per monomeric unit of a poly alpha-1,3-glucan ether compound. Alternatively, M.S. can refer to the average moles of etherification agent used to react with each monomeric unit in poly alpha-1,3-glucan (M.S. can thus describe the degree of derivatization of an etherification agent). It is noted that the M.S. value for poly alpha-1,3-glucan may have no upper limit. For example, when an organic group containing a hydroxyl group (e.g., hydroxyethyl or hydroxypropyl) has been etherified to poly alpha-1,3-glucan, the hydroxyl group of the organic group may undergo further reaction, thereby coupling more of the organic group to the poly alpha-1,3-glucan.

"Contacting" herein can be performed by any means known in the art, such as dissolving, mixing, shaking, or homogenization, for example.

The "molecular weight" of the poly alpha-1,3-glucan and poly alpha-1,3-glucan ether compounds herein can be represented as number-average molecular weight ($M_n$) or as weight-average molecular weight ($M_w$). Alternatively, molecular weight can be represented as Daltons, grams/mole, DPw (weight average degree of polymerization), or DPn (number average degree of polymerization). Various means are known in the art for calculating these molecular weight measurements, such as high-pressure liquid chromatography (HPLC), size exclusion chromatography (SEC), or gel permeation chromatography (GPC).

The terms "percent by volume", "volume percent", "vol %" and "v/v %" are used interchangeably herein. The percent by volume of a solute in a solution can be determined using the formula: [(volume of solute)/(volume of solution)]× 100%.

The terms "percent by weight", "weight percentage (wt %)" and "weight-weight percentage (% w/w)" are used interchangeably herein. Percent by weight refers to the percentage of a material on a mass basis as it is comprised in a composition, mixture or solution.

The terms "increased", "enhanced" and "improved" are used interchangeably herein. These terms refer to a greater quantity or activity such as a quantity or activity slightly greater than the original quantity or activity, or a quantity or activity in large excess compared to the original quantity or activity, and including all quantities or activities in between. Alternatively, these terms may refer to, for example, a quantity or activity that is at least 1%, 2%, 3%, 4%, 5%, 6%, 7%, 8%, 9%, 10%, 20%, 30%, 40%, 50%, 60%, 70%, 80%, 90%, 100%, 125%, 150%, 175%, or 200% (or any integer between 1% and 200%) more than the quantity or activity for which the increased quantity or activity is being compared.

Embodiments of the disclosed invention concern a composition comprising a poly alpha-1,3-glucan ether compound represented by the structure:

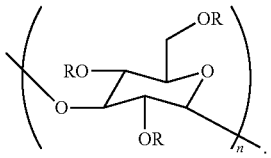

Regarding the formula of this structure, n can be at least 6, and each R can independently be an H or an organic group. Furthermore, the poly alpha-1,3-glucan ether compound has a degree of substitution of about 0.05 to about 3.0. Significantly, a poly alpha-1,3-glucan ether compound herein can be an alkyl ether and/or hydroxyalkyl ether derivative of poly alpha-1,3-glucan.

The degree of substitution (DoS) of a poly alpha-1,3-glucan ether compound disclosed herein can alternatively be about 0.2 to about 2.0. Alternatively still, the DoS can be at least about 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or 3.0. It would be understood by those skilled in the art that since a poly alpha-1,3-glucan ether compound disclosed herein has a degree of substitution between about 0.05 to about 3.0, and by virtue of being an ether, the R groups of the compound cannot only be hydrogen.

The percentage of glycosidic linkages between the glucose monomer units of the poly alpha-1,3-glucan ether compound that are alpha-1,3 is at least about 50%, 60%, 70%, 80%, 90%, 95%, 96%, 97%, 98%, 99%, or 100% (or any integer between 50% and 100%). In such embodiments, accordingly, the compound has less than about 50%, 40%, 30%, 20%, 10%, 5%, 4%, 3%, 2%, 1%, or 0% (or any integer value between 0% and 50%) of glycosidic linkages that are not alpha-1,3.

The backbone of a poly alpha-1,3-glucan ether compound disclosed herein is preferably linear/unbranched. In certain embodiments, the compound has no branch points or less than about 10%, 9%, 8%, 7%, 6%, 5%, 4%, 3%, 2%, or 1% branch points as a percent of the glycosidic linkages in the polymer. Examples of branch points include alpha-1,6 branch points.

The formula of a poly alpha-1,3-glucan ether compound in certain embodiments can have an n value of at least 6. Alternatively, n can have a value of at least 10, 50, 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, or 4000 (or any integer between 10 and 4000).

The molecular weight of a poly alpha-1,3-glucan ether compound disclosed herein can be measured as number-average molecular weight ($M_n$) or as weight-average molecular weight ($M_w$). Alternatively, molecular weight can be measured in Daltons or grams/mole. It may also be useful to refer to the $DP_w$ (weight average degree of polymerization) or $DP_n$ (number average degree of polymerization) of the poly alpha-1,3-glucan polymer component of the compound.

The $M_n$ or $M_w$ of poly alpha-1,3-glucan ether compounds disclosed herein may be at least about 1000. Alternatively, the $M_n$ or $M_w$ can be at least about 1000 to about 600000. Alternatively still, the $M_n$ or $M_w$ can be at least about 10000, 25000, 50000, 75000, 100000, 150000, 200000, 250000, 300000, 350000, 400000, 450000, 500000, 550000, or 600000 (or any integer between 10000 and 600000), for example.

Each R group in the formula of the poly alpha-1,3-glucan ether compound can independently be an H or an organic group. An organic group may be an alkyl group such as a methyl, ethyl, propyl, butyl, pentyl, hexyl, heptyl, octyl, nonyl, or decyl group, for example.

Alternatively, an organic group may be a substituted alkyl group in which there is a substitution on one or more carbons of the alkyl group. The substitution(s) may be one or more hydroxyl, aldehyde, ketone, and/or carboxyl groups. For example, a substituted alkyl group may be a hydroxy alkyl group, dihydroxy alkyl group, or carboxy alkyl group.

Examples of suitable hydroxy alkyl groups are hydroxymethyl (—CH$_2$OH), hydroxyethyl (e.g., —CH$_2$CH$_2$OH, —CH(OH)CH$_3$), hydroxypropyl (e.g., —CH$_2$CH$_2$CH$_2$OH, —CH$_2$CH(OH)CH$_3$, —CH(OH)CH$_2$CH$_3$), hydroxybutyl and hydroxypentyl groups. Other examples include dihydroxy alkyl groups (diols) such as dihydroxymethyl, dihydroxyethyl (e.g., —CH(OH)CH$_2$OH), dihydroxypropyl (e.g., —CH$_2$CH(OH)CH$_2$OH, —CH(OH)CH(OH)CH$_3$), dihydroxybutyl and dihydroxypentyl groups.

Examples of suitable carboxy alkyl groups are carboxymethyl (—CH$_2$COOH), carboxyethyl (e.g., —CH$_2$CH$_2$COOH, —CH(COOH)CH$_3$), carboxypropyl (e.g., —CH$_2$CH$_2$CH$_2$COOH, —CH$_2$CH(COOH)CH$_3$, —CH(COOH)CH$_2$CH$_3$), carboxybutyl and carboxypentyl groups.

Alternatively still, one or more carbons of an alkyl group can have a substitution(s) with another alkyl group. Examples of such substituent alkyl groups are methyl, ethyl and propyl groups. To illustrate, an R group can be —CH(CH$_3$)CH$_2$CH$_3$ or —CH$_2$CH(CH$_3$)CH$_3$, for example, which are both propyl groups having a methyl substitution.

As should be clear from the above examples of various substituted alkyl groups, a substitution (e.g., hydroxy or carboxy group) on an alkyl group in certain embodiments may be bonded to the terminal carbon atom of the alkyl group, where the terminal carbon group is opposite the terminus that is in ether linkage to the glucose group in the above formula. An example of this terminal substitution is the hydroxypropyl group —CH$_2$CH$_2$CH$_2$OH. Alternatively, a substitution may be on an internal carbon atom of an alkyl group. An example on an internal substitution is the hydroxypropyl group —CH$_2$CH(OH)CH$_3$. An alkyl group can have one or more substitutions, which may be the same (e.g., two hydroxyl groups [dihydroxy]) or different (e.g., a hydroxyl group and a carboxyl group).

Poly alpha-1,3-glucan ether compounds in certain embodiments disclosed herein may contain one type of organic group. For example, one or more R groups ether-linked to the glucose group in the above formula may be a methyl group; the R groups in this particular example would thus independently be hydrogen and methyl groups. Certain embodiments of poly alpha-1,3-glucan ether compounds containing only one type of organic group do not have a carboxy alkyl group (e.g., carboxymethyl group) as the organic group.

Alternatively, poly alpha-1,3-glucan ether compounds disclosed herein can contain two or more different types of organic groups. Examples of such compounds contain (i) two different alkyl groups as R groups, (ii) an alkyl group and a hydroxy alkyl group as R groups (alkyl hydroxyalkyl poly alpha-1,3-glucan, generically speaking), (iii) an alkyl group and a carboxy alkyl group as R groups (alkyl carboxyalkyl poly alpha-1,3-glucan, generically speaking), (iv) a hydroxy alkyl group and a carboxy alkyl group as R groups (hydroxyalkyl carboxyalkyl poly alpha-1,3-glucan, generically speaking), (v) two different hydroxy alkyl groups as R groups, or (vi) two different carboxy alkyl groups as R groups. Specific non-limiting examples of such compounds include ethyl hydroxyethyl poly alpha-1,3-glucan (i.e., where R groups are independently H, ethyl, or hydroxyethyl), hydroxyalkyl methyl poly alpha-1,3-glucan (i.e., where R groups are independently H, hydroxyalkyl, or methyl), carboxymethyl hydroxyethyl poly alpha-1,3-glucan (i.e., where R groups are independently H, carboxymethyl, or hydroxyethyl), and carboxymethyl hydroxypropyl poly alpha-1,3-glucan (i.e., where R groups are independently H, carboxymethyl, or hydroxypropyl). Certain embodiments of poly alpha-1,3-glucan ether compounds containing two or more different types of organic groups do not have a carboxy alkyl group (e.g., carboxymethyl group) as one of the organic groups.

The disclosed invention also concerns a method for producing a poly alpha-1,3-glucan ether compound. This method comprises: contacting poly alpha-1,3-glucan in a reaction under alkaline conditions with at least one etherification agent comprising an organic group, wherein the etherification agent is etherified to the poly alpha-1,3-glucan thereby producing a poly alpha-1,3-glucan ether compound represented by the structure:

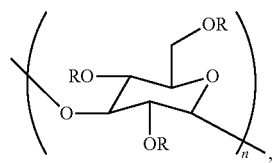

wherein
(i) n is at least 6,
(ii) each R is independently an H or the organic group, and
(iii) the compound has a degree of substitution of about 0.05 to about 3.0. A poly alpha-1,3-glucan ether produced by this method can optionally be isolated.

Poly alpha-1,3-glucan is contacted in a reaction under alkaline conditions with at least one etherification agent comprising an organic group. This step can be performed, for example, by first preparing alkaline conditions by contacting poly alpha-1,3-glucan with a solvent and one or more alkali hydroxides to provide a solution or mixture. The alkaline conditions of the reaction can thus comprise an alkali hydroxide solution. The pH of the alkaline conditions can be at least about 11.0, 11.2, 11.4, 11.6, 11.8, 12.0, 12.2, 12.4, 12.6, 12.8, or 13.0.

Various alkali hydroxides can be used, such as sodium hydroxide, potassium hydroxide, calcium hydroxide, lithium hydroxide, and/or tetraethylammonium hydroxide. The concentration of alkali hydroxide in a preparation with poly alpha-1,3-glucan and a solvent can be from about 1-70 wt %, 5-50 wt %, 10-50 wt %, 10-40 wt %, or 10-30 wt % (or any integer between 1 and 70 wt %). Alternatively, the concentration of alkali hydroxide such as sodium hydroxide can be at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 wt %. An alkali hydroxide used to prepare alkaline conditions may be in a completely aqueous solution or an aqueous solution comprising one or more water-soluble organic solvents such as ethanol or isopropanol. Alternatively, an alkali hydroxide can be added as a solid to provide alkaline conditions.

Various organic solvents that can optionally be included when preparing the reaction include alcohols, acetone, dioxane, isopropanol and toluene, for example; none of these solvents dissolve poly alpha-1,3-glucan. Toluene or isopropanol can be used in certain embodiments. An organic solvent can be added before or after addition of alkali hydroxide. The concentration of an organic solvent (e.g., isopropanol or toluene) in a preparation comprising poly alpha-1,3-glucan and an alkali hydroxide can be at least about 10, 15, 20, 25, 30, 35, 40, 45, 50, 55, 60, 65, 70, 75, 80, 85, or 90 wt % (or any integer between 10 and 90 wt %).

Alternatively, solvents that can dissolve poly alpha-1,3-glucan can be used when preparing the reaction. These solvents include, but are not limited to, lithium chloride(LiCl)/N,N-dimethyl-acetamide (DMAc), $SO_2$/diethylamine (DEA)/dimethyl sulfoxide (DMSO), LiCl/1,3-dimethy-2-imidazolidinone (DMI), N,N-dimethylformamide (DMF)/$N_2O_4$, DMSO/tetrabutyl-ammonium fluoride trihydrate (TBAF), N-methylmorpholine-N-oxide (NMMO), Ni(tren)(OH)$_2$ [tren¼tris(2-aminoethyl)amine] aqueous solutions and melts of $LiClO_4 \cdot 3H_2O$, NaOH/urea aqueous solutions, aqueous sodium hydroxide, aqueous potassium hydroxide, formic acid, and ionic liquids.

Poly alpha-1,3-glucan can be contacted with a solvent and one or more alkali hydroxides by mixing. Such mixing can be performed during or after adding these components with each other. Mixing can be performed by manual mixing, mixing using an overhead mixer, using a magnetic stir bar, or shaking, for example. In certain embodiments, poly alpha-1,3-glucan can first be mixed in water or an aqueous solution before it is mixed with a solvent and/or alkali hydroxide.

After contacting poly alpha-1,3-glucan, solvent, and one or more alkali hydroxides with each other, the resulting composition can optionally be maintained at ambient temperature for up to 14 days. The term "ambient temperature" as used herein refers to a temperature between about 15-30° C. or 20-25° C. (or any integer between 15 and 30° C.). Alternatively, the composition can be heated with or without reflux at a temperature from about 30° C. to about 150° C. (or any integer between 30 and 150° C.) for up to about 48 hours. The composition in certain embodiments can be heated at about 55° C. for about 30 minutes or 60 minutes. Thus, a composition obtained from mixing a poly alpha-1,3-glucan, solvent, and one or more alkali hydroxides with each other can be heated at about 50, 51, 52, 53, 54, 55, 56, 57, 58, 59, or 60° C. for about 30-90 minutes.

After contacting poly alpha-1,3-glucan, solvent, and one or more alkali hydroxides with each other, the resulting composition can optionally be filtered (with or without applying a temperature treatment step). Such filtration can be performed using a funnel, centrifuge, press filter, or any other method and/or equipment known in the art that allows removal of liquids from solids. Though filtration would remove much of the alkali hydroxide, the filtered poly alpha-1,3-glucan would remain alkaline (i.e., mercerized poly alpha-1,3-glucan), thereby providing alkaline conditions.

An etherification agent comprising an organic group is contacted with poly alpha-1,3-glucan in a reaction under alkaline conditions in a method herein of producing poly alpha-1,3-glucan ether compounds. For example, an etherification agent can be added to a composition prepared by contacting poly alpha-1,3-glucan, solvent, and one or more alkali hydroxides with each other as described above. Alternatively, an etherification agent can be included when preparing the alkaline conditions (e.g., an etherification agent can be mixed with poly alpha-1,3-glucan and solvent before mixing with alkali hydroxide).

An etherification agent herein refers to an agent that can be used to etherify one or more hydroxyl groups of the glucose units of poly alpha-1,3-glucan with an organic group as defined above. Examples of such organic groups include alkyl groups, hydroxy alkyl groups, and carboxy alkyl groups. One or more etherification agents may be used in the reaction.

Etherification agents suitable for preparing an alkyl poly alpha-1,3-glucan ether compound include, for example, dialkyl sulfates, dialkyl carbonates, alkyl halides (e.g., alkyl chloride), iodoalkanes, alkyl triflates (alkyl trifluoromethane-sulfonates) and alkyl fluorosulfonates. Thus, examples of etherification agents for producing methyl poly alpha-1,3-glucan ethers include dimethyl sulfate, dimethyl carbonate, methyl chloride, iodomethane, methyl triflate and methyl fluorosulfonate. Examples of etherification agents for producing ethyl poly alpha-1,3-glucan ethers include diethyl sulfate, diethyl carbonate, ethyl chloride, iodoethane, ethyl triflate and ethyl fluorosulfonate. Examples of etherification agents for producing propyl poly alpha-1,3-glucan ethers include dipropyl sulfate, dipropyl carbonate, propyl chloride, iodopropane, propyl triflate and propyl fluorosulfonate. Examples of etherification agents for producing butyl poly alpha-1,3-glucan ethers include dibutyl sulfate, dibutyl carbonate, butyl chloride, iodobutane and butyl triflate.

Etherification agents suitable for preparing a hydroxyalkyl poly alpha-1,3-glucan ether compound include, for example, alkylene oxides such as ethylene oxide, propylene oxide (e.g., 1,2-propylene oxide), butylene oxide (e.g., 1,2-butylene oxide; 2,3-butylene oxide; 1,4-butylene oxide), or combinations thereof. As examples, propylene oxide can be used as an etherification agent for preparing hydroxypropyl poly alpha-1,3-glucan, and ethylene oxide can be used as an etherification agent for preparing hydroxyethyl poly alpha-1,3-glucan. Alternatively, hydroxyalkyl halides (e.g., hydroxyalkyl chloride) can be used as etherification agents for preparing hydroxyalkyl poly alpha-1,3-glucan. Examples of hydroxyalkyl halides include hydroxyethyl halide, hydroxypropyl halide (e.g., 2-hydroxypropyl chloride, 3-hydroxypropyl chloride) and hydroxybutyl halide. Alternatively, alkylene chlorohydrins can be used as etherification agents for preparing hydroxyalkyl poly alpha-1,3-glucan. Alkylene chlorohydrins that can be used include, but are not limited to, ethylene chlorohydrin, propylene chlorohydrin, butylene chlorohydrin, or combinations of these.

Etherification agents suitable for preparing a dihydroxyalkyl poly alpha-1,3-glucan ether compound include dihydroxyalkyl halides (e.g., dihydroxyalkyl chloride) such as dihydroxyethyl halide, dihydroxypropyl halide (e.g., 2,3-dihydroxypropyl chloride [i.e., 3-chloro-1,2-propanediol]), or dihydroxybutyl halide, for example. 2,3-dihydroxypropyl chloride can be used to prepare dihydroxypropyl poly alpha-1,3-glucan, for example.

Etherification agents suitable for preparing a carboxyalkyl poly alpha-1,3-glucan ether compound may include haloalkylates (e.g., chloroalkylate). Examples of haloalkylates include haloacetate (e.g., chloroacetate), 3-halopropionate (e.g., 3-chloropropionate) and 4-halobutyrate (e.g., 4-chlorobutyrate). For example, chloroacetate (monochloroacetate) (e.g., sodium chloroacetate) can be used as an etherification agent to prepare carboxymethyl poly alpha-1,3-glucan.

When producing a poly alpha-1,3-glucan ether compound with two or more different organic groups, two or more different etherification agents would be used, accordingly. For example, both an alkylene oxide and an alkyl chloride could be used as etherification agents to produce an alkyl hydroxyalkyl poly alpha-1,3-glucan ether. Any of the etherification agents disclosed herein may therefore be combined to produce poly alpha-1,3-glucan ether compounds with two or more different organic groups. Such two or more etherification agents may be used in the reaction at the same time, or may be used sequentially in the reaction. When used sequentially, any of the temperature-treatment (e.g., heating) steps disclosed below may optionally be used between each addition. One may choose sequential introduction of etherification agents in order to control the desired DoS of each organic group. In general, a particular etherification agent would be used first if the organic group it forms in the ether product is desired at a higher DoS compared to the DoS of another organic group to be added.

The amount of etherification agent to be contacted with poly alpha-1,3-glucan in a reaction under alkaline conditions can be determined based on the degree of substitution required in the poly alpha-1,3-glucan ether compound being produced. The amount of ether substitution groups on each monomeric unit in poly alpha-1,3-glucan ether compounds produced herein can be determined using nuclear magnetic resonance (NMR) spectroscopy. The molar substitution (MS) value for poly alpha-1,3-glucan has no upper limit. In general, an etherification agent can be used in a quantity of at least about 0.05 mole per mole of poly alpha-1,3-glucan. There is no upper limit to the quantity of etherification agent that can be used.

Reactions for producing poly alpha-1,3-glucan ether compounds herein can optionally be carried out in a pressure vessel such as a Parr reactor, an autoclave, a shaker tube or any other pressure vessel well known in the art. A shaker tube is used to perform the reaction in certain embodiments.

A reaction herein can optionally be heated following the step of contacting poly alpha-1,3-glucan with an etherification agent under alkaline conditions. The reaction temperatures and time of applying such temperatures can be varied within wide limits. For example, a reaction can optionally be maintained at ambient temperature for up to 14 days. Alternatively, a reaction can be heated, with or without reflux, between about 25° C. to about 200° C. (or any integer between 25 and 200° C.). Reaction time can be varied correspondingly: more time at a low temperature and less time at a high temperature.

In certain embodiments of producing hydroxypropyl poly alpha-1,3-glucan, a reaction can be heated to about 75° C. for about 3 hours. A reaction for preparing hydroxyethyl poly alpha-1,3-glucan can be heated to about 60° C. for about 6 hours, for example. Thus, a reaction for preparing a hydroxyalkyl poly alpha-1,3-glucan herein can optionally be heated to about 55° C. to about 80° C. (or any integer between 55 and 80° C.) for about 2 hours to about 7 hours, for example.

In certain embodiments of producing methyl poly alpha-1,3-glucan, a reaction can be heated to about 55° C. or 70° C. for about 17 hours. A reaction for preparing ethyl poly alpha-1,3-glucan can be heated to about 90° C. for about 17 hours, for example. Thus, a reaction mixture for preparing an alkyl poly alpha-1,3-glucan herein can be heated to about 55° C. to about 95° C. (or any integer between 55 and 95° C.) for about 15 hours to about 20 hours, for example.

In certain embodiments of producing carboxymethyl poly alpha-1,3-glucan, a reaction can be heated to about 55° C. for about 3 hours. Thus, a reaction for preparing a carboxyalkyl poly alpha-1,3-glucan herein can be heated to about 50° C. to about 60° C. (or any integer between 50 and 60° C.) for about 2 hours to about 5 hours, for example.

In certain embodiments of producing dihydroxyalkyl (e.g., dihydroxypropyl) poly alpha-1,3-glucan ether, poly alpha-1,3 glucan is added to an alkali hydroxide solution (e.g., tetraethylammonium hydroxide) (e.g., about 20 wt % solution) to a final concentration or mass contribution of poly alpha-1,3 glucan of about 4, 5, 6, 7, or 8 wt % (e.g., ~6.5 wt %). After heating/stirring steps to dissolve the poly alpha-1,3 glucan, an appropriate etherification agent (e.g., a dihydroxyalkyl chloride such as 2,3-dihydroxypropyl chloride) may be added to a final concentration of about 7, 8, 9, 10, or 11 wt % (e.g., ~9.5 wt %). The resulting reaction can be held at about 50° C. to about 60° C. (or any integer between 50 and 60° C., e.g., 55° C.) for about 1.5-2.5 hours (e.g. about 2 hours), for example, before neutralizing the reaction. Water-soluble dihydroxyalkyl poly alpha-1,3-glucan can be produced by employing these steps.

Optionally, a reaction herein can be maintained under an inert gas, with or without heating. As used herein, the term "inert gas" refers to a gas which does not undergo chemical reactions under a set of given conditions, such as those disclosed for preparing a reaction herein.

All of the components of the reactions disclosed herein can be mixed together at the same time and brought to the desired reaction temperature, whereupon the temperature is maintained with or without stirring until the desired poly alpha-1,3-glucan ether compound is formed. Alternatively, the mixed components can be left at ambient temperature as described above.

Following etherification, the pH of a reaction can be neutralized. Neutralization of a reaction can be performed using one or more acids. The term "neutral pH" as used herein, refers to a pH that is neither substantially acidic or basic (e.g., a pH of about 6-8, or about 6.0, 6.2, 6.4, 6.6, 6.8, 7.0, 7.2, 7.4, 7.6, 7.8, or 8.0). Various acids that can be used for this purpose include, but are not limited to, sulfuric, acetic, hydrochloric, nitric, any mineral (inorganic) acid, any organic acid, or any combination of these acids.

A poly alpha-1,3-glucan ether compound produced in a reaction herein can optionally be washed one or more times with a liquid that does not readily dissolve the compound. For example, poly alpha-1,3-glucan ether can be washed with water, alcohol, acetone, aromatics, or any combination of these, depending on the solubility of the ether compound therein (where lack of solubility is desirable for washing). In general, a solvent comprising an organic solvent such as alcohol is preferred for washing a poly alpha-1,3-glucan ether. A poly alpha-1,3-glucan ether product can be washed one or more times with an aqueous solution containing methanol or ethanol, for example. For example, 70-95 wt % ethanol can be used to wash the product. A poly alpha-1,3-glucan ether product can be washed with a methanol:acetone (e.g., 60:40) solution in another embodiment. Hot water (about 95-100° C.) can be used in certain embodiments, such as for washing alkyl poly alpha-1,3-glucan ethers (e.g., ethyl poly alpha-1,3-glucan) and alkyl hydroxyalkyl poly alpha-1,3-glucan ethers (e.g., ethyl hydroxyethyl poly alpha-1,3-glucan).

A poly alpha-1,3-glucan ether produced in the disclosed reaction can be isolated. This step can be performed before or after neutralization and/or washing steps using a funnel, centrifuge, press filter, or any other method or equipment known in the art that allows removal of liquids from solids. For example, a Buchner funnel may be used to isolate a poly alpha-1,3-glucan ether product. An isolated poly alpha-1,3-glucan ether product can be dried using any method known in the art, such as vacuum drying, air drying, or freeze drying.

Any of the above etherification reactions can be repeated using a poly alpha-1,3-glucan ether product as the starting material for further modification. This approach may be suitable for increasing the DoS of an organic group, and/or adding one or more different organic groups to the ether product. For example, a dihydroxypropyl poly alpha-1,3-glucan ether product can be used as a substrate for further modification with dihydroxypropyl groups.

The structure, molecular weight and degree of substitution of a poly alpha-1,3-glucan ether product can be confirmed using various physiochemical analyses known in the art such as NMR spectroscopy and size exclusion chromatography (SEC).

The percentage of glycosidic linkages between the glucose monomer units of poly alpha-1,3-glucan used to prepare poly alpha-1,3-glucan ether compounds herein that are alpha-1,3 is at least about 50%, 60%, 70%, 80%, 90%, 95%, 96%, 97%, 98%, 99%, or 100% (or any integer value between 50% and 100%). In such embodiments, accordingly, poly alpha-1,3-glucan has less than about 50%, 40%, 30%, 20%, 10%, 5%, 4%, 3%, 2%, 1%, or 0% (or any integer value between 0% and 50%) of glycosidic linkages that are not alpha-1,3.

Poly alpha-1,3-glucan used to prepare poly alpha-1,3-glucan ether compounds herein is preferably linear/unbranched. In certain embodiments, poly alpha-1,3-glucan has no branch points or less than about 10%, 9%, 8%, 7%, 6%, 5%, 4%, 3%, 2%, or 1% branch points as a percent of the glycosidic linkages in the polymer. Examples of branch points include alpha-1,6 branch points.

The $M_n$ or $M_w$ of poly alpha-1,3-glucan used to prepare poly alpha-1,3-glucan ether compounds herein may be at least about 500 to about 300000. Alternatively still, $M_n$ or $M_w$ can be at least about 10000, 25000, 50000, 75000, 100000, 125000, 150000, 175000, 200000, 225000, 250000, 275000, or 300000 (or any integer between 10000 and 300000), for example.

As disclosed above, poly alpha-1,3-glucan used for preparing poly alpha-1,3-glucan ether compounds herein can be enzymatically produced from sucrose using one or more glucosyltransferase (gtf) enzymes. The poly alpha-1,3-glucan product of this enzymatic reaction can be purified before using it to prepare an ether using the disclosed process. Alternatively, a poly alpha-1,3-glucan product of a gtf reaction can be used with little or no processing for preparing poly alpha-1,3-glucan ether compounds.

A poly alpha-1,3-glucan slurry can be used directly in any of the above processes for producing a poly alpha-1,3-glucan ether compound disclosed herein. As used herein, a "poly alpha-1,3-glucan slurry" refers to a mixture comprising the components of a gtf enzymatic reaction. A gtf enzymatic reaction can include, in addition to poly alpha-1,3-glucan itself, various components such as sucrose, one or more gtf enzymes, glucose, fructose, leucrose, buffer, FermaSure®, soluble oligosaccharides, oligosaccharide primers, bacterial enzyme extract components, borates, sodium hydroxide, hydrochloric acid, cell lysate, proteins and/or nucleic acids. Minimally, the components of a gtf enzymatic reaction can include, in addition to poly alpha-1,3-glucan itself, sucrose, one or more gtf enzymes, glucose and fructose, for example. In another example, the components of a gtf enzymatic reaction can include, in addition to poly alpha-1,3-glucan itself, sucrose, one or more gtf enzymes, glucose, fructose, leucrose and soluble oligosaccharides (and optionally bacterial enzyme extract components). It should be apparent that poly alpha-1,3-glucan, when in a slurry as disclosed herein, has not been purified or washed. It should also be apparent that a slurry represents a gtf enzymatic reaction that is complete or for which an observable amount of poly alpha-1,3-glucan has been produced, which forms a solid since it is insoluble in the aqueous reaction milieu (has pH of 5-7, for example). A poly alpha-1,3-glucan slurry can be prepared by setting up a gtf reaction as disclosed in U.S. Pat. No. 7,000,000 or U.S. Patent Appl. Publ. Nos. 2013/0244288 and 2013/0244287, for example, all of which are incorporated herein by reference. A poly alpha-1,3-glucan slurry can be entered, for example, into a reaction for producing a carboxyalkyl poly alpha-1,3-glucan such as carboxymethyl poly alpha-1,3-glucan.

Alternatively, a wet cake of poly alpha-1,3-glucan can be used directly in any of the above processes for producing a poly alpha-1,3-glucan ether compound disclosed herein. A "wet cake of poly alpha-1,3-glucan" as used herein refers to poly alpha-1,3-glucan that has been separated (e.g., filtered) from a slurry and washed with water or an aqueous solution. A wet cake can be washed at least 1, 2, 3, 4, 5, or more times, for example. The poly alpha-1,3-glucan is not dried when preparing a wet cake. A wet cake is termed as "wet" given the retention of water by the washed poly alpha-1,3-glucan.

A wet cake of poly alpha-1,3-glucan can be prepared using any device known in the art for separating solids from liquids, such as a filter or centrifuge. For example, poly alpha-1,3-glucan solids in a slurry can be collected on a Buchner funnel using a mesh screen over filter paper. Filtered wet cake can be resuspended in water (e.g., deionized water) and filtered one or more times to remove soluble components of the slurry such as sucrose, fructose and leucrose. As another example for preparing a wet cake, poly alpha-1,3-glucan solids from a slurry can be collected as a pellet via centrifugation, resuspended in water (e.g., deionized water), and re-pelleted and resuspended one or more additional times. A poly alpha-1,3-glucan wet cake can be entered into a reaction for producing any ether compound herein, such as carboxyalkyl poly alpha-1,3-glucan (e.g., carboxymethyl poly alpha-1,3-glucan).

EXAMPLES

The disclosed invention is further defined in the following Examples. It should be understood that these Examples, while indicating certain preferred aspects of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

Materials

Acetone, sodium hydroxide, acetic acid, and isopropanol were from EMD Chemicals (Billerica, Mass.). Methyl chloride, acetic acid, toluene, dimethyl sulfate, ethanol and propylene oxide were from Sigma Aldrich (St. Louis, Mo.). Methanol and 2-propanol were from BDH Chemicals (Poole Dorset, UK).

Preparation of Poly Alpha-1,3-Glucan

Poly alpha-1,3-glucan was prepared using a gtfJ enzyme preparation as described in U.S. Patent Appl. Publ. No. 2013/0244288, which is incorporated herein by reference in its entirety.

$^1$H Nuclear Magnetic Resonance (NMR) Method for Determining Molar Substitution of Poly Alpha-1,3-Glucan Ether Derivatives Approximately 30 mg of the poly alpha-1,3-glucan ether derivative was weighed into a vial on an analytical balance. The vial was removed from the balance and 1.0 mL of deuterium oxide was added to the vial. A magnetic stir bar was added to the vial and the mixture was stirred to suspend the solid. Deuterated sulfuric acid (50% v/v in $D_2O$), 1.0 mL, was then added to the vial and the mixture was heated at 90° C. for 1 hour in order to depolymerize and solubilize the polymer. The solution was allowed to cool to room temperature and then a 0.8 mL portion of the solution was transferred into a 5-mm NMR tube using a glass pipet. A quantitative $^1$H NMR spectrum was acquired using an Agilent VNMRS 400 MHz NMR spectrometer equipped with a 5-mm Autoswitchable Quad probe. The spectrum was acquired at a spectral frequency of 399.945 MHz, using a spectral window of 6410.3 Hz, an acquisition time of 3.744 seconds, an inter-pulse delay of 10 seconds and 64 pulses. The time domain data were transformed using exponential multiplication of 0.50 Hz.

Two regions of the resulting spectrum were integrated for NMR analysis of hydroxypropyl poly alpha-1,3-glucan: an integral from 1.1 ppm to 1.4 ppm, representative of the three methyl protons of all isopropyl groups present; and an integral from 4.7 ppm to 5.6 ppm, representative of the anomeric protons of the glucose rings. The integral of the isopropyl methyl region was divided by 3 to obtain a measure of the $OCH_2CH(CH_3)O$ groups that were present. The molar substitution by the $OCH_2CH(CH_3)O$ groups was then calculated by dividing the measure of the $OCH_2CH(CH_3)O$ groups by the measure of all glucose rings present (the integral value of the anomeric protons).

Two regions of the resulting spectrum were integrated for NMR analysis of methyl poly alpha-1,3-glucan: an integral from 3.0 ppm to 4.2 ppm was representative of the six glucan protons plus the $OCH_3$ protons, and an integral from 4.6 ppm to 5.6 ppm was representative of the anomeric protons of the glucose rings. The integral of this latter region was multiplied by six to obtain the integral of the other six glucan protons. The calculated integral for the six non-anomeric glucan protons was subtracted from the integral of the 3.0 ppm to 4.2 ppm region to obtain the integral contribution of the $OCH_3$ protons. This integral value was divided by 3.0 to obtain a measure of the $OCH_3$ groups that are present. The degree of methylation was then calculated by dividing the measure of the $OCH_3$ groups by the measure of all glucose rings present (the integral value of the anomeric protons).

Regarding NMR analysis of carboxymethyl poly alpha-1,3-glucan, the chemical shifts of the lines in the spectrum were referenced to the signal for the alpha anomeric protons with no substitution at the $C_2OH$. This signal should be the third group of peaks from the left most edge of the spectrum. The left-most signal in this group of peaks was set to 5.222 ppm. Five regions of the referenced spectrum were integrated: an integral from 5.44 ppm to 4.60 ppm represents all of the anomeric protons; the integrals from 4.46 ppm to 4.41 ppm and from 4.36 ppm to 4.32 ppm were from the carboxymethyl $CH_2$ at the $C_2$ position adjacent to either alpha or beta C1HOH; the integral from 4.41 ppm to 4.36 ppm is from the carboxymethyl $CH_2$ at the C4 position; and the integral from 4.24 ppm to 4.17 ppm was from the carboxymethyl $CH_2$ at the C6 position. The degree of carboxymethylation at the 2, 4, and 6 positions was then calculated by dividing the integrals for the $OCH_2COOH$ groups by two and then dividing those results by the integration for all of the anomeric protons. A total degree of substitution was obtained by adding together the three individual degrees of substitution.

Determination of the Degree of Polymerization

The degree of polymerization (DP) was determined by size exclusion chromatography (SEC). For SEC analysis, dry poly alpha-1,3-glucan ether derivative was dissolved in phosphate-buffered saline (PBS) (0.02-0.2 mg/mL). The chromatographic system used was an Alliance™ 2695 liquid chromatograph from Waters Corporation (Milford, Mass.) coupled with three on-line detectors: a differential refractometer 410 from Waters, a multi-angle light-scattering photometer Heleos™ 8+ from Wyatt Technologies (Santa Barbara, Calif.), and a differential capillary viscometer ViscoStar™ from Wyatt Technologies. The columns used for SEC were two Tosoh Haas Bioscience TSK $GMPW_{XL}$ g3K and g4K G3000PW and G4000PW polymeric columns for aqueous polymers. The mobile phase was PBS. The chromatographic conditions used were 30° C. at column and detector compartments, 30° C. at sample and injector compartments, a flow rate of 0.5 mL/min, and injection volume of 100 µL. The software packages used for data reduction were Astra version 6 from Wyatt (triple detection method with column calibration).

Example 1

Preparation of Hydroxypropyl Poly Alpha-1,3-Glucan

This Example describes producing the glucan ether derivative, hydroxypropyl poly alpha-1,3-glucan.

10 g of poly alpha-1,3-glucan (number-average molecular weight $[M_n]$=71127) was mixed with 101 g of toluene and 5 mL of 20% sodium hydroxide. This preparation was stirred in a 500-mL glass beaker on a magnetic stir plate at 55° C. for 30 minutes. The preparation was then transferred to a shaker tube reactor after which 34 g of propylene oxide was added; the reaction was then stirred at 75° C. for 3 hours. The reaction was then neutralized with 20 g of acetic acid and the hydroxypropyl poly alpha-1,3-glucan solids thus formed were filtered with a Buchner funnel. The solids were then washed in a beaker with 70% ethanol and dried in a vacuum oven with a slight nitrogen bleed until constant dryness was achieved. The molar substitution (MS) of the dried product was reported by NMR to be 3.89.

Thus, the glucan ether derivative, hydroxypropyl poly alpha-1,3-glucan, was prepared and isolated.

Example 2

Preparation of Hydroxyethyl Poly Alpha-1,3-Glucan

This Example describes producing the glucan ether derivative, hydroxyethyl poly alpha-1,3-glucan.

10 g of poly alpha-1,3-glucan ($M_n$=71127) was mixed with 150 mL of isopropanol and 40 mL of 30% sodium hydroxide. This preparation was stirred in a 500-mL glass beaker on a magnetic stir plate at 55° C. for 1 hour, and then stirred overnight at ambient temperature. The preparation was then transferred to a shaker tube reactor after which 15 g of ethylene oxide was added; the reaction was then stirred at 60° C. for 6 hour. The reaction was then allowed to remain in the sealed shaker tube overnight (approximately 16 hours) before it was neutralized with 20.2 g of acetic acid thereby forming hydroxyethyl poly alpha-1,3-glucan solids. The solids were filtered using a Buchner funnel with 35-micrometer filter paper. The solids were then washed in a beaker by adding a methanol:acetone (60:40 v/v) mixture and stirring with a stir bar for 20 minutes. The methanol:acetone mixture was then filtered away from the solids. This washing step was repeated two times. The solids, which had a slightly brown/beige color, were dried in a vacuum oven with a nitrogen bleed. The hydroxyethyl poly alpha-1,3-glucan product was soluble in a 10% NaOH solution. The MS of the dried product was reported by NMR to be 0.72.

Thus, the glucan ether derivative, hydroxyethyl poly alpha-1,3-glucan, was prepared and isolated.

Example 3

Preparation of Ethyl Poly Alpha-1,3-Glucan

This Example describes producing the glucan ether derivative, ethyl poly alpha-1,3-glucan.

Poly alpha-1,3-glucan is added to a shaker tube, after which sodium hydroxide (1-70% solution) and ethyl chloride are added to provide a reaction. The reaction is heated to 25-200° C. and held at that temperature for 1-48 hours before the reaction is neutralized with acetic acid. The solid thus formed is collected by vacuum filtration and washed, dried under a vacuum at 20-25° C., and analyzed by NMR and SEC to determine the molecular weight and degree of substitution (DoS) of the ethyl poly alpha-1,3-glucan.

Thus, the glucan ether derivative, ethyl poly alpha-1,3-glucan, is prepared and isolated.

Example 4

Preparation of Ethyl Hydroxyethyl Poly Alpha-1,3-Glucan

This Example describes producing the glucan ether derivative, ethyl hydroxyethyl poly alpha-1,3-glucan.

Poly alpha-1,3-glucan is added to a shaker tube, after which sodium hydroxide (1-70% solution) is added. Then, ethyl chloride is added followed by an ethylene oxide/ethyl chloride mixture to provide a reaction. The reaction is slowly heated to 25-200° C. and held at that temperature for 1-48 hours before being neutralized with acetic acid. The solid thus formed is collected by vacuum filtration and washed with hot water, dried under a vacuum at 20-70° C., and analyzed by NMR and SEC to determine the molecular weight and DoS of the ethyl hydroxyethyl poly alpha-1,3-glucan.

Thus, the glucan ether derivative, ethyl hydroxyethyl poly alpha-1,3-glucan, is prepared and isolated.

Example 5

Preparation of Methyl Poly Alpha-1,3-Glucan

This Example describes producing the glucan ether derivative, methyl poly alpha-1,3-glucan.

10 g of poly alpha-1,3-glucan ($M_n$=71127) was mixed with 40 mL of 30% sodium hydroxide and 40 mL of 2-propanol, and stirred at 55° C. for 1 hour to provide alkali poly alpha-1,3-glucan. This preparation was then filtered using a Buchner funnel. The alkali poly alpha-1,3-glucan was then mixed with 150 mL of 2-propanol to make a slurry. A shaker tube reactor was charged with this slurry and 15 g of methyl chloride was added to provide a reaction. The reaction was stirred at 70° C. for 17 hours. The resulting methyl poly alpha-1,3-glucan solid was filtered and neutralized with 20 mL 90% acetic acid, followed by three 200-mL ethanol washes. NMR analysis was performed, indicating that the DoS of the methyl poly alpha-1,3-glucan product was 1.2.

Table 1 provides a list of DoS measurements for various samples of methyl poly alpha-1,3-glucan prepared using methods having certain modifications compared to the above method (refer to Table 1). The mercerization step (alkali treatment of poly alpha-1,3-glucan prior to addition of methylating reagent) for each of the processes listed in Table 1 was conducted for 1 hour, as above.

TABLE 1

Preparation of Methyl Poly Alpha-1,3-Glucan Using Various Mercerization and Methylation Conditions

| Mercerization conditions | | | Methylation conditions | | | |
|---|---|---|---|---|---|---|
| Glucan $M_n$ | Temp (° C.) | Solvent | Reagent | Time (hours) | Temp (° C.) | DoS |
| 71127 | RT | Toluene (140 mL) | DMS[a] (50 mL) | 17 | 50 | 1.51 |
| 71127 | 55 | 2-propanol (150 mL) | CH$_3$Cl (15 g) | 17 | 70 | 1.2 |
| 71127 | 55 | 2-propanol (150 mL) | CH$_3$Cl (25 g) | 24 | 70 | 1.38 |
| 25084 | 55 | 2-propanol (150 mL) | CH$_3$Cl (30 g) | 34 | 70 | 1.0 |
| 25084 | 55 | 2-propanol (150 mL) | CH$_3$Cl (25 g) | 24 | 70 | 0.39 |

[a]Dimethyl sulfate

Thus, the glucan ether derivative, methyl poly alpha-1,3-glucan, was prepared and isolated.

Example 6

Preparation of Water-Soluble Methyl Poly Alpha-1,3-Glucan

This Example describes producing water-soluble methyl poly alpha-1,3-glucan.

10 g of methyl poly alpha-1,3-glucan (DoS=1.38) as prepared in Example 5 (Table 1) was mixed with 40 mL of 30% sodium hydroxide and 40 mL of 2-propanol and stirred at 55° C. for 1 hour. This mixture was then filtered using a Buchner funnel. 150 mL of 2-propanol was added to make a slurry, which was then placed into a shaker tube reactor. 15 g of methyl chloride was added to the slurry to provide a reaction. The reaction was stirred at 55° C. for 17 hours, after which it was neutralized with 10 mL of acetic acid and mixed with 200 mL of acetone to precipitate the product. The product was then washed with two additional 200-mL acetone washes. NMR analysis of the methyl poly alpha-1,3-glucan product indicated that it had a DoS of 2.

A solution of the methyl poly alpha-1,3-glucan product in water was prepared by dissolving 0.2 g of the product in 9.8 g water and mixing at room temperature. A clear solution was formed thereby indicating that the methyl poly alpha-1,3-glucan product was water-soluble.

Thus, water-soluble methyl poly alpha-1,3-glucan was prepared and isolated.

Example 7

Preparation of Hydroxyalkyl Methyl Poly Alpha-1,3-Glucan

This Example describes producing the glucan ether derivative, hydroxyalkyl methyl poly alpha-1,3-glucan.

Poly alpha-1,3-glucan is added to a vessel, after which sodium hydroxide (5-70% solution) is added. This preparation is stirred for 0.5-8 hours. Then, methyl chloride is added to the vessel to provide a reaction, which is then heated to 30-100° C. for up to 14 days. An alkylene oxide (e.g., ethylene oxide, propylene oxide, butylene oxide, etc.) is then added to the reaction while controlling the temperature. The reaction is heated to 25-100° C. for up to 14 days before being neutralized with acid. The solid product thus formed is filtered, washed and dried.

Thus, the glucan ether derivative, hydroxyalkyl methyl poly alpha-1,3-glucan, is prepared and isolated. Depending on the alkylene oxide used after the methylation step, examples of this derivative include hydroxyethyl methyl poly alpha-1,3-glucan, hydroxypropyl methyl poly alpha-1,3-glucan, and hydroxybutyl methyl poly alpha-1,3-glucan.

Example 8

Preparation of Carboxymethyl Hydroxyethyl Poly Alpha-1,3-Glucan

This Example describes producing the glucan ether derivative, carboxymethyl hydroxyethyl poly alpha-1,3-glucan.

Poly alpha-1,3-glucan is added to an aliquot of a substance such as isopropanol or toluene in a 400-mL capacity shaker tube, after which sodium hydroxide (1-70% solution) is added. This preparation is stirred for up to 48 hours. Then, monochloroacetic acid is added to provide a reaction, which is then heated to 25-100° C. for up to 14 days. Ethylene oxide is then added to the reaction, which is then heated to 25-100° C. for up to 14 days before being neutralized with acid (e.g., acetic, sulfuric, nitric, hydrochloric, etc.). The solid product thus formed is collected by vacuum filtration, washed and dried.

Thus, the glucan ether derivative, carboxymethyl hydroxyethyl poly alpha-1,3-glucan, is prepared and isolated.

Example 9

Preparation of Sodium Carboxymethyl Hydroxyethyl Poly Alpha-1,3-Glucan

This Example describes producing the glucan ether derivative, sodium carboxymethyl hydroxyethyl poly alpha-1,3-glucan.

Poly alpha-1,3-glucan is added to an aliquot of an alcohol such as isopropanol in a 400-mL capacity shaker tube, after which sodium hydroxide (1-70% solution) is added. This preparation is stirred for up to 48 hours. Then, sodium monochloroacetate is added to provide a reaction, which is then heated to 25-100° C. for up to 14 days. Ethylene oxide is then added to the reaction, which is then heated to 25-100° C. for up to 14 days before being neutralized with acid (e.g., acetic, sulfuric, nitric, hydrochloric, etc.). The solid product thus formed is collected by vacuum filtration, washed and dried.

Thus, the glucan ether derivative, sodium carboxymethyl hydroxyethyl poly alpha-1,3-glucan, is prepared and isolated.

Example 10

Preparation of Carboxymethyl Hydroxypropyl Poly Alpha-1,3-Glucan

This Example describes producing the glucan ether derivative, carboxymethyl hydroxypropyl poly alpha-1,3-glucan.

Poly alpha-1,3-glucan is added to an aliquot of a substance such as isopropanol or toluene in a 400-mL capacity shaker tube, after which sodium hydroxide (1-70% solution) is added. This preparation is stirred for up to 48 hours. Then, monochloroacetic acid is added to provide a reaction, which is then heated to 25-100° C. for up to 14 days. Propylene oxide is then added to the reaction, which is then heated to 25-100° C. for up to 14 days before being neutralized with acid (e.g., acetic, sulfuric, nitric, hydrochloric, etc.). The solid product thus formed is collected by vacuum filtration, washed and dried.

Thus, the glucan ether derivative, carboxymethyl hydroxypropyl poly alpha-1,3-glucan, is prepared and isolated.

Example 11

Preparation of Sodium Carboxymethyl Hydroxypropyl Poly Alpha-1,3-Glucan

This Example describes producing the glucan ether derivative, sodium carboxymethyl hydroxypropyl poly alpha-1,3-glucan.

Poly alpha-1,3-glucan is added to an aliquot of a substance such as isopropanol or toluene in a 400-mL capacity shaker tube, after which sodium hydroxide (1-70% solution) is added. This preparation is stirred for up to 48 hours. Then, sodium monochloroacetate is added to provide a reaction, which is then heated to 25-100° C. for up to 14 days. Propylene oxide is then added to the reaction, which is then heated to 25-100° C. for up to 14 days before being neutralized with acid (e.g., acetic, sulfuric, nitric, hydrochloric, etc.). The solid product thus formed is collected by vacuum filtration, washed and dried.

Thus, the glucan ether derivative, sodium carboxymethyl hydroxypropyl poly alpha-1,3-glucan, is prepared and isolated.

Example 12

Preparation of Poly Alpha-1,3-Glucan Slurry and Wet Cake Using GtfJ Enzyme

This Example describes producing a slurry or a wet cake of poly alpha-1,3-glucan using a reaction catalyzed by the a glucosyltransferase enzyme, gtfJ. These compositions were used in Examples 13 and 14 to prepare poly alpha-1,3-glucan ether compounds.

Additional information regarding gtfJ enzyme can be found in U.S. Pat. No. 7,000,000 and U.S. Patent Appl. Publ. Nos. 2013/0244288 and 2013/0244287 (all of which are incorporated herein by reference).

To prepare a slurry of poly alpha-1,3-glucan, an aqueous solution (0.75 L) containing sucrose (100 g/L), potassium phosphate buffer (20 mM), and FermaSure® (500 ppm) was prepared and adjusted to pH 6.8-7.0. This solution was then charged with gtfJ enzyme extract (50 units/L). The enzyme reaction solution was maintained at 20-25° C. for 48 hours. A slurry was formed since the poly alpha-1,3-glucan synthesized in the reaction was aqueous insoluble. This slurry was then used, without any filtration, to prepare carboxymethyl poly alpha-1,3-glucan (see Example 13).

The gtfJ enzyme reaction was performed as above to prepare a poly alpha-1,3-glucan wet cake. The poly alpha-1,3-glucan solids produced in the reaction were collected using a Buchner funnel fitted with a 325-mesh screen over 40-micrometer filter paper. The filtered poly alpha-1,3-glucan solids were resuspended in deionized water and filtered twice more as above to remove sucrose, fructose and other low molecular weight, soluble by-products. The wet cake of poly alpha-1,3-glucan solids was then used to prepare carboxymethyl poly alpha-1,3-glucan (see Example 14).

Thus, a slurry and a wet cake of poly alpha-1,3-glucan were prepared. These types of poly alpha-1,3-glucan preparations can be used as substrates for preparing poly alpha-1,3-glucan ether compounds.

Example 13

Preparation of Carboxymethyl Poly Alpha-1,3-Glucan from Poly Alpha-1,3-Glucan Slurry This Example describes producing the ether compound, carboxymethyl poly alpha-1,3-glucan, using a slurry of poly alpha-1,3-glucan as prepared in Example 12. This slurry was not filtered or washed, and so comprised components of the glucosyltransferase reaction used to synthesize the poly alpha-1,3-glucan.

Poly alpha-1,3-glucan slurry (500 g) was placed in a 1-L jacketed reaction vessel fitted with a thermocouple for temperature monitoring, a condenser connected to a recirculating bath, and a magnetic stir bar. Solid sodium hydroxide (75 g) was added to the slurry to yield a preparation with 15 wt % sodium hydroxide. This preparation was heated to 25° C. on a hotplate. The preparation was then stirred for 1 hour before the temperature was increased to 55° C. Sodium chloroacetate (227.3 g) was added to the preparation and the reaction temperature was held at 55° C. for 3 hours. The reaction was then neutralized with acetic acid (90%). The solid was collected by vacuum filtration and washed with ethanol (70%) four times, dried under vacuum at 20-25° C., and analyzed by NMR and SEC to determine molecular weight and DoS. The solid material obtained was identified as water-soluble carboxymethyl poly alpha-1,3-glucan with a DoS of 0.3 and a $M_w$ of 140,000.

Thus, a slurry of poly alpha-1,3-glucan containing components of a glucosyltransferase reaction can be used as a substrate for preparing poly alpha-1,3-glucan ether compounds. This result indicates that the products of a glucosyltransferase reaction used to synthesize poly alpha-1,3-glucan do not require any processing (such as washing or purifying the poly alpha-1,3-glucan product) before being used in reactions to produce poly alpha-1,3-glucan ether compounds.

Example 14

Preparation of Carboxymethyl Poly Alpha-1,3-Glucan from Poly Alpha-1,3-Glucan Wet Cake This Example describes producing the ether compound, carboxymethyl poly alpha-1,3-glucan, using a wet cake of poly alpha-1,3-glucan as prepared in Example 12. This wet cake was not dried before its use in this Example.

Poly alpha-1,3-glucan wet cake (500 g) was placed in a 1-L jacketed reaction vessel fitted with a thermocouple for temperature monitoring, a condenser connected to a recirculating bath, and an overhead stirrer. Isopropanol (500 mL) and solid sodium hydroxide (79.1 g) were added to the wet cake to yield a preparation with 15 wt % sodium hydroxide. This preparation was heated to 25° C. on a hotplate, and then stirred for 1 hour before the temperature was increased to 55° C. Sodium chloroacetate (227.3 g) was added to the preparation and the reaction temperature was held at 55° C. for 3 hours. The reaction was then neutralized with acetic acid (90%). The solids were collected by vacuum filtration and washed with ethanol (70%) four times, dried under vacuum at 20-25° C., and analyzed by NMR and SEC to determine molecular weight and DoS. The solid material obtained was identified as water-soluble carboxymethyl poly alpha-1,3-glucan with a DoS of 0.7 and a $M_w$ of 250,000.

Thus, a wet cake of poly alpha-1,3-glucan can be used as a substrate for preparing poly alpha-1,3-glucan ether compounds. This result indicates that the poly alpha-1,3-glucan product of a glucosyltransferase reaction can be used with little processing (washing with water) in reactions for producing poly alpha-1,3-glucan ether compounds.

Example 15

Preparation of Sodium Carboxymethyl Poly Alpha-1,3-Glucan

This Example describes producing the glucan ether derivative, sodium carboxymethyl poly alpha-1,3-glucan.

10 g of poly alpha-1,3-glucan ($M_w$ [weight-average molecular weight]=236,854) was added to 200 mL of isopropanol in a 500-mL capacity round bottom flask fitted with a thermocouple for temperature monitoring and a condenser connected to a recirculating bath, and a magnetic stir bar. 40 mL of sodium hydroxide (15% solution) was added dropwise to the preparation, which was then heated to 25° C. on a hotplate. The preparation was stirred for 1 hour before the temperature was increased to 55° C. Sodium chloroacetate (12 g) was then added to provide a reaction, which was held at 55° C. for 3 hours before being neutralized with 90% acetic acid. The solid thus formed was collected by vacuum filtration and washed with ethanol (70%) four times, dried under vacuum at 20-25° C., and analyzed by NMR and SEC to determine molecular weight and DoS. The solid material obtained was identified as water-soluble sodium carboxymethyl poly alpha-1,3-glucan with a DoS of 0.5 and an $M_w$ of 580,000.

Table 2 provides a list of DoS measurements for various samples of sodium carboxymethyl poly alpha-1,3-glucan prepared using the above method. The poly alpha-1,3-glucan starting material had various molecular weights (Table 2).

TABLE 2

DoS of Sodium Carboxymethyl Poly Alpha-1,3-Glucan Prepared from Poly Alpha-1,3-Glucan

| CMG Sample Designation | $M_w$ of poly alpha-1,3-glucan starting material | DoS |
| --- | --- | --- |
| 1A (35) | 140287 | 0.5 |
| 1B (36) | 140287 | 0.9 |

TABLE 2-continued

DoS of Sodium Carboxymethyl Poly Alpha-1,3-Glucan
Prepared from Poly Alpha-1,3-Glucan

| CMG Sample Designation | $M_w$ of poly alpha-1,3- glucan starting material | DoS |
|---|---|---|
| 1C (39) | 140287 | 1 |
| 1D (44) | 88445 | 0.7 |
| 1E (47) | 278858 | 0.7 |
| 1F (58) | 248006 | |
| 1G (67) | 236854 | 0.5 |
| 1H (72) | 236854 | 0.9 |
| 1I (−41) | 200000 | 0.5 |
| 1J (−39) | 168584 | 0.5 |

Thus, the glucan ether derivative, sodium carboxymethyl poly alpha-1,3-glucan, was prepared and isolated.

Example 16

Preparation of Potassium Carboxymethyl Poly Alpha-1,3-Glucan

This Example describes producing the glucan ether derivative, potassium carboxymethyl poly alpha-1,3-glucan.

10 g of poly alpha-1,3-glucan ($M_w$=168,000) was added to 200 mL of isopropanol in a 500-mL capacity round bottom flask fitted with a thermocouple for temperature monitoring and a condenser connected to a recirculating bath, and a magnetic stir bar. 40 mL of potassium hydroxide (15% solution) was added dropwise to this preparation, which was then heated to 25° C. on a hotplate. The preparation was stirred for 1 hour before the temperature was increased to 55° C. Sodium chloroacetate (12 g) was then added to provide a reaction, which was held at 55° C. for 3 hours before being neutralized with 90% acetic acid. The solid thus formed was collected by vacuum filtration and washed with ethanol (70%) four times, dried under vacuum at 20-25° C., and analyzed by NMR and SEC to determine molecular weight and DoS. The solid material obtained was identified as water soluble potassium carboxymethyl poly alpha-1,3-glucan with a DoS of 0.77.

Thus, the glucan ether derivative, potassium carboxymethyl poly alpha-1,3-glucan, was prepared and isolated.

Example 17

Preparation of Lithium Carboxymethyl Poly Alpha-1,3-Glucan

This Example describes producing the glucan ether derivative, lithium carboxymethyl poly alpha-1,3-glucan.

10 g of poly alpha-1,3-glucan ($M_w$=168,000) was added to 200 mL of isopropanol in a 500-mL capacity round bottom flask fitted with a thermocouple for temperature monitoring and a condenser connected to a recirculating bath, and a magnetic stir bar. 50 mL of lithium hydroxide (11.3% solution) was added dropwise to this preparation, which was then heated to 25° C. on a hotplate. The preparation was stirred for 1 hour before the temperature was increased to 55° C. Sodium chloroacetate (12 g) was then added to provide a reaction, which was held at 55° C. for 3 hours before being neutralized with 90% acetic acid. The solid thus formed was collected by vacuum filtration and washed with ethanol (70%) four times, dried under vacuum at 20-25° C., and analyzed by NMR and SEC to determine molecular weight and DoS. The solid material obtained was identified as water soluble CMG with a DoS of 0.79.

Reagent amounts were adjusted to prepare another CMG sample, which had a DoS of 0.36. The CMG samples prepared in this Example are listed in Table 3.

TABLE 3

Lithium CMG Synthesis

| Sample designation | DoS |
|---|---|
| 2A (127) | 0.79 |
| 2B (130) | 0.36 |

Thus, the glucan ether derivative, lithium carboxymethyl poly alpha-1,3-glucan, was prepared and isolated.

Example 18

Preparation of Methyl Poly Alpha-1,3-Glucan

This Example describes producing the glucan ether derivative, methyl poly alpha-1,3-glucan (MG). This Example is in addition to Example 5, which describes the production of MG.

Sample 1

10 g of poly alpha-1,3-glucan ($M_w$=168584) was added to 40 mL of isopropanol and 40 mL of 30 wt % sodium hydroxide in a 400-mL beaker with a magnetic stir bar. The beaker was stirred on a magnetic stir plate at 375 rpm for one hour. The solid from this preparation was then collected by vacuum filtration, mixed with 150 mL of isopropanol, and placed in a 200-mL capacity jar with a lid. This preparation sat overnight before being transferred to a 250-mL capacity shaker tube reactor. The reactor was heated to 70° C. and charged with 10 g of methyl chloride. The reaction was held at temperature for 17 hours and then charged with an additional 20 g of methyl chloride and held at temperature for 17 hours. After cooling, the reaction was neutralized with 90% acetic acid. The solid from this reaction was collected by vacuum filtration, washed with methanol three times, dried under vacuum at 20-25° C., and analyzed by NMR to determine DoS. The solid material obtained was identified as MG with a DoS of 1.75.

8 g of this MG was then mixed with 50 mL isopropanol and 32 mL of 30 wt % sodium hydroxide in a 400-mL beaker with a magnetic stir bar. The beaker was stirred on a magnetic stir plate at 375 rpm for one hour. The solid was then collected by vacuum filtration, mixed with 150 mL of isopropanol, and placed in a 200-mL capacity jar with a lid. This preparation sat overnight before being transferred to a 250-mL capacity shaker tube reactor. The reactor was heated to 70° C. and charged with 12 g of methyl chloride. After cooling, the reaction was neutralized with 90% acetic acid. The solid was collected by vacuum filtration and washed with methanol: acetone (60:40) five times, dried under vacuum at 20-25° C., and analyzed by NMR to determine DoS. The solid material obtained was identified as MG with a DoS of 1.8. This MG was denoted as Sample 1.

Sample 2

20 g of poly alpha-1,3-glucan ($M_w$=245,000) was added to 50 mL of isopropanol and 80 mL of 30 wt % sodium hydroxide in a 400-mL beaker with a magnetic stir bar. The beaker was stirred on a magnetic stir plate at 375 rpm for one hour. The solid from this preparation was then collected by vacuum filtration, mixed with 150 mL of isopropanol, and placed in a 200-mL capacity jar with a lid. This preparation sat overnight before being transferred to a 250-mL capacity shaker tube reactor. The reactor was heated to 70° C. and charged with 30 g of methyl chloride. The reaction was held at temperature for 17 hours. After cooling, the reaction was neutralized with 90% acetic acid. The solid from this reaction was collected by vacuum filtration, washed with methanol:acetone (60:40) five times, dried under vacuum at 20-25° C., and analyzed by NMR to determine DoS. The solid material obtained was identified as MG with a DoS of 1.39.

10 g of this MG was then mixed with 50 mL isopropanol and 40 mL of 30 wt % sodium hydroxide solution in a 400-mL beaker with a magnetic stir bar. The beaker was stirred on a magnetic stir plate at 375 rpm for one hour. The solid from this preparation was then collected by vacuum filtration, mixed with 100 mL of isopropanol, and placed in a 200-mL capacity jar with a lid. This preparation sat overnight before being transferred to a 250-mL capacity shaker tube reactor. The reactor was heated to 70° C. and charged with 15 g of methyl chloride. After cooling, the reaction was neutralized with 90% acetic acid. The solid was collected by vacuum filtration and washed with methanol:acetone (60:40) five times, dried under vacuum at 20-25° C., and analyzed by NMR to determine DoS. The solid material obtained was identified as MG. This MG was denoted as Sample 2.

Thus, additional samples of the glucan ether derivative, methyl poly alpha-1,3-glucan, were prepared and isolated.

Example 19

Preparation of Ethyl Poly Alpha-1,3-Glucan

This Example describes producing the glucan ether derivative, ethyl poly alpha-1,3-glucan (EG). This Example is in addition to Example 3, which describes a method for producing EG.

20 g of poly alpha-1,3-glucan ($M_w$=245,000) was added to 200 mL of isopropanol and 109 mL of 15 wt % sodium hydroxide in a 400-mL beaker with a magnetic stir bar. The beaker was stirred on a magnetic stir plate at 375 rpm for one hour. The solid from this preparation was then collected by vacuum filtration, mixed with 100 mL of acetone, and placed in a 200-mL capacity jar with a lid. This preparation sat overnight before being transferred to a 250-mL capacity shaker tube reactor. The reactor was heated to 90° C. and charged with 85 g of ethyl chloride. The reaction was held at temperature for 17 hours. After cooling, the reaction was neutralized with 90% acetic acid. The solid was collected by vacuum filtration, washed with 80% acetone five times, dried under vacuum at 20-25° C., and analyzed by NMR to determine DoS. The solid material obtained was identified as EG with a DoS of 1.03.

Thus, the glucan ether derivative, ethyl poly alpha-1,3-glucan, was prepared and isolated.

Example 20

Preparation of Hydroxypropyl Poly Alpha-1,3-Glucan

This Example describes producing the glucan ether derivative, hydroxypropyl poly alpha-1,3-glucan (HPG). This Example is in addition to Example 1, which describes a method for producing HPG.

10 g of poly alpha-1,3-glucan ($M_w$=168584) was added to 101 mL of toluene and 5 mL of 20 wt % sodium hydroxide in a 400-mL beaker with a magnetic stir bar. The beaker was stirred on a magnetic stir plate at 375 rpm for one hour at 55° C. This preparation was then placed in a 200-mL capacity jar with a lid and allowed to sit overnight before being transferred to a 250-mL capacity shaker tube reactor. The reactor was heated to 75° C. and charged with 34 g of 1,2-propylene oxide. The reaction was held at temperature for 4 hours. After cooling, the reaction was neutralized with 90% acetic acid. The solid was collected by vacuum filtration, washed with hot water three times, dried under vacuum at 20-25° C., and analyzed by NMR to determine DoS. The solid material was determined to be HPG.

Thus, additional samples of the glucan ether derivative, hydroxypropyl poly alpha-1,3-glucan, were prepared and isolated.

Example 21

Preparation of a Dihydroxyalkyl Poly Alpha-1,3-Glucan

This Example describes producing a dihydroxyalkyl ether derivative of poly alpha-1,3-glucan. Specifically, dihydroxypropyl poly alpha-1,3-glucan was produced.

10 g of poly alpha-1,3-glucan ($M_w$=138,438) was added to 100 mL of 20% tetraethylammonium hydroxide in a 500-mL capacity round bottom flask fitted with a thermocouple for temperature monitoring and a condenser connected to a recirculating bath, and a magnetic stir bar (resulting in ~9.1 wt % poly alpha-1,3-glucan). This preparation was stirred and heated to 30° C. on a hotplate. The preparation was stirred for 1 hour to dissolve the solid before the temperature was increased to 55° C. 3-chloro-1,2-propanediol (6.7 g) and 11 g of DI water were then added to provide a reaction (containing ~5.2 wt % 3-chloro-1,2-propanediol), which was held at 55° C. for 1.5 hours afterwhich time 5.6 g of DI water was added to the reaction. The reaction was held at 55° C. for an additional 3 hours and 45 minutes before being neutralized with acetic acid. After neutralization, an excess of isopropanol was added to precipitate a solid. The solid thus formed was collected by vacuum filtration and washed with ethanol (95%) four times, and dried under vacuum at 20-25° C. The solid material obtained was identified as dihydroxypropyl poly alpha-1,3-glucan that was not water soluble, and having a degree of substitution of 0.6.

The above procedure was repeated with some modification, and this time using a sample of the dihydroxypropyl poly alpha-1,3-glucan prepared above as the starting material. Briefly, 5 g of the glucan ether was added to 50 mL of 20% tetraethylammonium hydroxide. This preparation was stirred with a magnetic stir bar until the solid dissolved, and then heated to 30° C. for 1 hour on a hotplate. The preparation was then heated to 55° C. and 3-chloro-1,2-propanediol (8 g) was added to provide a reaction. The reaction was then stirred for 2 hours, afterwhich time it was neutralized with acetic acid. After neutralization, an excess of isopropanol was added to precipitate a solid. The solid thus formed was collected by vacuum filtration and washed with ethanol (95%) four times, and dried under vacuum at 20-25° C. The solid material obtained was identified as dihydroxypropyl poly alpha-1,3-glucan that was water soluble, and having a degree of substitution of 0.89.

Thus, a water-soluble dihydroxyalkyl ether derivative of poly alpha-1,3-glucan was prepared and isolated.

Example 22

Preparation of a Dihydroxyalkyl Poly Alpha-1,3-Glucan

This Example describes producing dihydroxypropyl poly alpha-1,3-glucan. This Example is in addition to Example 21, which also describes producing this glucan ether derivative.

10 g of poly alpha-1,3-glucan ($M_w$=138,438) was added to 143 g of 20% tetraethylammonium hydroxide in a 500-mL capacity round bottom flask fitted with a thermocouple for temperature monitoring and a condenser connected to a recirculating bath, and a magnetic stir bar (resulting in ~6.5 wt % poly alpha-1,3-glucan). This preparation was stirred and heated to 30° C. on a hotplate. The preparation was stirred for 1 hour to dissolve the solid before the temperature was increased to 55° C. 3-chloro-1,2-propanediol (16 g) was then added to provide a reaction (containing ~9.5 wt % 3-chloro-1,2-propanediol), which was held at 55° C. for 2 hours before being neutralized with acetic acid. After neutralization, an excess of isopropanol was added to precipitate a solid. The solid thus formed was collected by vacuum filtration and washed with ethanol (95%) four times, and dried under vacuum at 20-25° C. The solid material obtained was identified as dihydroxypropyl poly alpha-1,3-glucan that was water soluble, and having a degree of substitution of 0.6.

Thus, a water-soluble dihydroxyalkyl ether derivative of poly alpha-1,3-glucan was prepared and isolated. It is noted that, even though the dihydroxypropyl poly alpha-1,3-glucan produced in this example had a degree of substitution of 0.6, it was water-soluble. This result is in contrast with the dihydroxypropyl poly alpha-1,3-glucan produced in the first process described in Example 21 above, which also had a degree of substitution of 0.6, but was water-insoluble.

What is claimed is:

1. A composition comprising a poly alpha-1,3-glucan ether compound represented by the structure:

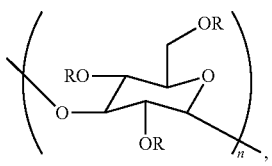

wherein
  (i) n is at least 800,
  (ii) each R is independently an H or an organic group, and
  (iii) the compound has a degree of substitution of about 0.05 to about 3.0, and the compound contains two or more types of said organic group.

2. The composition of claim 1, wherein said organic group is a hydroxy alkyl group, alkyl group, or carboxy alkyl group.

3. The composition of claim 2, wherein said organic group is a hydroxypropyl, dihydroxypropyl, hydroxyethyl, methyl, ethyl, or carboxymethyl group.

4. The composition of claim 1, wherein the degree of substitution is about 0.2 to about 2.0.

5. A method of producing a poly alpha-1,3-glucan ether compound, the method comprising:
  (a) contacting poly alpha-1,3-glucan in a reaction under alkaline conditions with at least one etherification agent comprising an organic group, wherein the etherification agent is etherified to the poly alpha-1,3-glucan thereby producing a poly alpha-1,3-glucan ether compound represented by the structure:

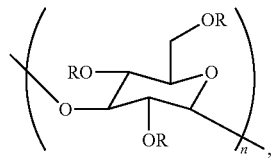

wherein
  (i) n is at least 800,
  (ii) each R is independently an H or the organic group, and
  (iii) the compound has a degree of substitution of about 0.05 to about 3.0, and the compound contains two or more types of said organic group; and
  (b) optionally, isolating the poly alpha-1,3-glucan ether compound produced in step (a).

6. The method of claim 5, wherein said alkaline conditions comprise an alkali hydroxide solution.

7. The method of claim 5, wherein the reaction comprises an organic solvent.

8. The method of claim 5, wherein step (a) further comprises:
  (i) heating the reaction; and/or
  (ii) neutralizing the pH of the reaction.

9. The method of claim 5, wherein said organic group is a hydroxy alkyl group, alkyl group, or carboxy alkyl group.

10. The method of claim 5, wherein the poly alpha-1,3-glucan is in a form of a slurry.

11. The method of claim 10, wherein the slurry comprises poly alpha-1,3-glucan, sucrose, glucose, fructose and a glucosyltransferase enzyme.

12. The method of claim 5, wherein the poly alpha-1,3-glucan is in a form of a wet cake.

13. The composition of claim 1, wherein n is at least 900.

14. The composition of claim 13, wherein n is at least 1000.

15. The composition of claim 1, wherein the percentage of glycosidic linkages of the poly alpha-1,3-glucan ether compound that are alpha-1,3 is at least 99%.

16. The composition of claim 15, wherein the percentage of glycosidic linkages of the poly alpha-1,3-glucan ether compound that are alpha-1,3 is 100%.

17. The method of claim 5, wherein n is at least 1000.

18. The method of claim 5, wherein the percentage of glycosidic linkages of the poly alpha-1,3-glucan ether compound that are alpha-1,3 is 100%.

* * * * *